(12) United States Patent
Schlachter

(10) Patent No.: US 11,766,332 B2
(45) Date of Patent: Sep. 26, 2023

(54) IMPLANTABLE MESH

(71) Applicant: Warsaw Orthopedic, Inc., Warsaw, IN (US)

(72) Inventor: Kelly W. Schlachter, Mason, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 333 days.

(21) Appl. No.: 17/031,331

(22) Filed: Sep. 24, 2020

(65) Prior Publication Data

US 2021/0000603 A1 Jan. 7, 2021

Related U.S. Application Data

(62) Division of application No. 15/219,376, filed on Jul. 26, 2016.

(51) Int. Cl.
*A61F 2/28* (2006.01)
*A61L 27/56* (2006.01)
(Continued)

(52) U.S. Cl.
CPC ............ *A61F 2/2846* (2013.01); *A61L 27/02* (2013.01); *A61L 27/3608* (2013.01); *A61L 27/56* (2013.01);
(Continued)

(58) Field of Classification Search
CPC .......... A61L 27/12; A61L 27/24; A61L 27/50; A61L 27/58; A61L 27/54; A61L 27/3608;
(Continued)

(56) References Cited

U.S. PATENT DOCUMENTS 8,591,531 B2   11/2013   Buevich et al.
8,740,987 B2   6/2014   Geremakis et al.
(Continued)

FOREIGN PATENT DOCUMENTS

CN   1403167 A   3/2003
CN   101365499 A   2/2009
(Continued)

OTHER PUBLICATIONS

Milin Patel et al., "Needle Punching Technology", The Maharaja Sayajirao Univ of Baroda, Vadodara; Feb. 19, 2010; 10 pp.
(Continued)

*Primary Examiner* — William H Matthews
(74) *Attorney, Agent, or Firm* — Sorell, Lenna & Schmidt, LLP; William D. Schmidt

(57) ABSTRACT

An implantable mesh including demineralized bone fibers mechanically entangled into a biodegradable or permanent implantable mesh is provided. A method of preparing the implantable mesh is also provided. The method of preparing the implantable mesh includes mechanically entangling demineralized bone fibers with non-bone fibers to form the implantable mesh. The mechanical entanglement of the bone fibers into the implantable mesh is achieved by applying needle punching with barbed needles, spun lacing, entanglement with water jets or air jets or ultrasonic entanglement with ultrasonic waves. A method of implanting an implantable mesh at a target bone tissue site is also provided.

15 Claims, 3 Drawing Sheets

(51) Int. Cl.
*A61L 27/36* (2006.01)
*A61L 27/02* (2006.01)

(52) U.S. Cl.
CPC ............ *A61F 2002/2817* (2013.01); *A61F 2210/0004* (2013.01); *A61F 2230/0067* (2013.01); *A61F 2230/0069* (2013.01); *A61F 2310/00011* (2013.01); *A61F 2310/00161* (2013.01); *A61F 2310/00359* (2013.01); *A61F 2310/00371* (2013.01); *A61L 2430/02* (2013.01)

(58) Field of Classification Search
CPC .. A61L 27/56; A61L 2400/06; A61L 2430/06; A61F 2/28; A61F 2/2846; A61F 2/4601; A61F 2/0811; A61F 2210/0004; A61F 2002/30062; A61F 2002/2817; A61F 2002/2835
See application file for complete search history.

(56) References Cited

U.S. PATENT DOCUMENTS

| | | | |
|---|---|---|---|
| 8,877,221 B2 * | 11/2014 | McKay | ............ A61L 27/54 514/16.7 |
| 8,992,965 B2 | 3/2015 | Behnam | |
| 9,011,543 B2 | 4/2015 | Trieu et al. | |
| 9,814,577 B2 | 11/2017 | Ralph et al. | |
| 2005/0283255 A1 * | 12/2005 | Geremakis | ............ B29C 67/02 606/76 |
| 2008/0077252 A1 | 3/2008 | Mills et al. | |
| 2009/0157087 A1 | 6/2009 | Wei et al. | |
| 2010/0196333 A1 | 8/2010 | Gaskins et al. | |
| 2013/0189338 A1 | 7/2013 | Drapeau et al. | |
| 2014/0031795 A1 | 1/2014 | McKay | |
| 2014/0046350 A1 | 2/2014 | Buevich et al. | |
| 2014/0200676 A1 | 7/2014 | Shimko et al. | |
| 2014/0212471 A1 | 7/2014 | Drapeau et al. | |
| 2014/0220142 A1 | 8/2014 | Song et al. | |
| 2015/0126090 A1 | 5/2015 | Nelson et al. | |
| 2015/0297793 A1 | 10/2015 | McKay | |
| 2015/0306278 A1 * | 10/2015 | McKay | ............ A61L 27/56 264/28 |

FOREIGN PATENT DOCUMENTS

| | | |
|---|---|---|
| CN | 101754730 A | 6/2010 |
| CN | 103957952 A | 7/2014 |
| EP | 1216717 B1 | 8/2010 |
| WO | 2013109663 A1 | 7/2013 |

OTHER PUBLICATIONS

M.G. Kamath et al., "Spunlace (Hydroentanglement)"; Apr. 2004; 20 pp.

Batra et al., "INDA Nonwovens Glossary"; Associate of the Nonwoven Fabrics Industry; 2002; pp. 1-64.

European Search Report and Opinion, a foreign counterpart of the present application dated Dec. 21, 2017, 7 pages.

Office Action dated Feb. 3, 2021 issued by the Chinese Patent Office in corresponding Chinese Application No. 201710614989.9 for Implantable Mesh.

* cited by examiner

IMPLANTABLE MESH

BACKGROUND

It is estimated that more than half a million bone grafting procedures are performed in the United States annually with a cost over $2.5 billion. These numbers are expected to double by 2020. Both natural bone and bone substitutes have been used as graft materials. Natural bone may be autograft or allograft. Bone substitutes include natural or synthetic materials such as collagen, silicone, acrylics, calcium phosphate, calcium sulfate, or the like.

There are at least three ways in which a bone graft can help repair a bone defect. The first is osteogenesis, the formation of new bone within the graft by the presence of bone-forming cells called osteoprogenitor cells. The second is osteoinduction, a process in which molecules contained within the graft (e.g., bone morphogenic proteins and other growth factors) convert progenitor cells into bone-forming cells. The third is osteoconduction, a physical effect by which a matrix often containing graft material acts as a scaffold on which bone and cells in the recipient are able to form. The scaffolds promote the migration, proliferation and differentiation of bone cells for bone regeneration.

Bone fiber based-demineralized bone matrices for implantation exhibit improvements in mechanical properties, including cohesiveness, fiber length, fiber diameter or width, fiber aspect ratio, or a combination of multiple variables.

Demineralized bone matrices (DBMs) have been shown to exhibit the ability to induce and/or conduct the formation of bone. It is therefore desirable to implant and maintain a demineralized bone matrix at a site where bone growth is desired. Some DBMs are available as putties, gels, pastes, or in some specific shapes, for example sheets. In some cases DBM sheets do not have sufficient integrity for some applications and can be pulled apart when implanted into bone defects that are not easily confined. Oftentimes, when DBM fibers are made they lack cohesiveness and tend to fall apart or become loose in the package or during processing. In order to reduce this tendency, a carrier (for example, glycerol) is commonly added to keep the DBM fibers together. The inclusion of a carrier can lead to additional manufacturing expenses and further complicate regulatory approval processes.

Therefore, there is a need for DBM compositions and methods that allow osteogenesis, osteoinduction and/or osteoconduction and at the same time, have sufficient integrity to wrap around a bone defect, help contain other allograft, autograft and/or synthetic graft material and can accept sutures therein without fear of tearing apart. DBM compositions and methods that can be reinforced by a resorbable or non-resorbable mesh that do not need a carrier would be beneficial. Furthermore, reinforced DBM compositions and methods that easily allow hydration of the demineralized bone matrix would also be beneficial.

SUMMARY

An implantable mesh including demineralized bone fibers mechanically entangled into the implantable mesh is provided. In some embodiments, the implantable mesh comprises a demineralized bone fiber mechanically entangled with a biodegradable mesh fiber; in other embodiments, the implantable mesh comprises a plurality of biodegradable mesh fibers mechanically entangled with each other that are then mechanically entangled with one or more demineralized bone fibers; in yet other embodiments, the implantable mesh comprises biodegradable fibers mechanically entangled with the demineralized bone fibers to form a plurality of layers in the implantable mesh.

In various embodiments, the implantable mesh further includes an osteinductive and/or osteopromotive additive including a bone marrow aspirant, blood, a blood product, a bone morphogenetic protein, a growth factor disposed on the biodegradable mesh fiber. In certain embodiments, the implantable mesh further includes a therapeutic agent or mixtures thereof. In other aspects, the implantable mesh includes collagen fibers mechanically entangled into the mesh. In certain embodiments, the implantable mesh can include non-bone fibers, for example, chips, shards, particles and/or shavings, which are of a sufficient configuration to become mechanically entangled with the biodegradable or permanent mesh.

In certain embodiments, the bone fibers become mechanically entangled into the implantable mesh by needle punching with barbed needles, entanglement with water or air jets, ultrasonic entanglement with ultrasonic waves. In other embodiments, the implantable mesh containing demineralized bone fibers mechanically entangled into it is further subjected to moisture, heat and/or pressure provided by pressure rollers. In some embodiments, the implantable mesh containing mechanically entangled demineralized bone fibers is lyophilized.

In various embodiments, the implantable mesh containing demineralized bone fibers mechanically entangled therein includes autograft or allograft bone. In some embodiments, the implantable mesh containing demineralized bone fibers mechanically entangled therein contains woven or nonwoven bone fibers. The demineralized bone fibers can have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In some embodiments, the demineralized bone fibers have a diameter from about 100 μm to about 2 mm. In other embodiments, the demineralized bone fibers have a length from about 0.5 cm to about 10 cm.

In certain embodiments, a method of preparing an implantable mesh is provided. The method comprises mechanically entangling demineralized bone fibers with non-bone fibers to form the implantable mesh. In other embodiments, the mechanical entangling comprises applying to the demineralized bone fibers and the non-bone fibers needle punching with barbed needles, spun lacing, entanglement with water jets or air jets or ultrasonic entanglement with ultrasonic waves. In various aspects, the implantable mesh does not contain a carrier or adhesive.

In some embodiments, a method of treating a target bone tissue site is provided. The method of treatment includes contacting the bone tissue site with the implantable mesh, the implantable mesh comprising demineralized bone fibers mechanically entangled into the implantable mesh. In other embodiments, the method of treatment further includes contacting the implantable mesh with a liquid and molding the mechanically entangled demineralized bone material into a shape which is configured to fit at, near or in the target bone tissue site. The liquid useful for contacting the implantable mesh containing demineralized bone fiber mechanically entangled therein, in various aspects, includes physiologically acceptable water, physiological saline, sodium chloride, dextrose, Lactated Ringer's solution, phosphate buffered saline, blood, bone marrow aspirate, bone marrow fractions or a combination thereof in an amount sufficient to render the implantable osteogenic material moldable. In some embodiments, the implantable mesh is configured to be wrapped around the target bone tissue site. In other embodiments, the implantable mesh can be secured with sutures to the target bone tissue site without tearing upon removal.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
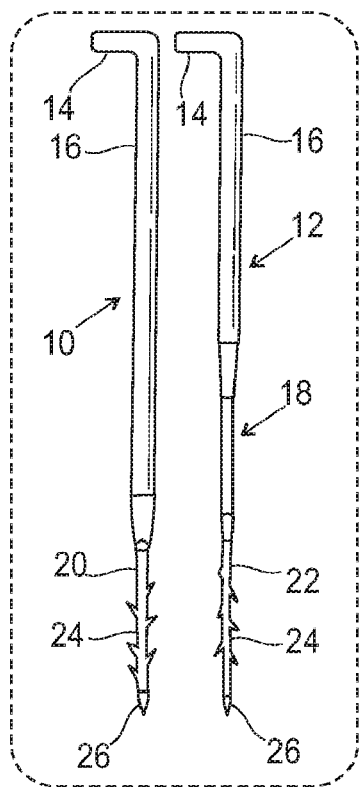
FIG. 1 depicts two barbed needles used in needle punching technology.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of promoting an understanding of the principles of the disclosure, reference will now be made to certain embodiments and specific language will be used to describe the same. It will nevertheless be understood that no limitation of the scope of the disclosure is thereby intended, such alterations and further modifications in the illustrated bone material, and such further applications of the principles of the disclosure as described herein being contemplated as would normally occur to one skilled in the art to which the disclosure relates.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below:

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "an allograft" includes one, two, three or more allografts.

The terms "bioactive" composition or "pharmaceutical" composition as used herein may be used interchangeably. Both terms refer to compositions that can be administered to a subject. Bioactive or pharmaceutical compositions are sometimes referred to herein as "pharmaceutical compositions" or "bioactive compositions" of the current disclosure.

The term "biodegradable" includes that all or parts of the carrier and/or implant will degrade over time by the action of enzymes, by hydrolytic action and/or by other similar mechanisms in the human body. In various embodiments, "biodegradable" includes that the carrier and/or implant can break down or degrade within the body to non-toxic components after or while a therapeutic agent has been or is being released. By "bioerodible" it is meant that the carrier and/or implant will erode or degrade over time due, at least in part, to contact with substances found in the surrounding tissue, fluids or by cellular action.

The term "mammal" refers to organisms from the taxonomy class "mammalian" including, but not limited to, humans; other primates such as chimpanzees, apes, orangutans and monkeys; rats, mice, cats, dogs, cows, horses, etc.

A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired. In some embodiments the implant is designed for immediate release. In other embodiments the implant is designed for sustained release. In other embodiments, the implant comprises one or more immediate release surfaces and one or more sustained release surfaces.

The terms "treating" and "treatment" when used in connection with a disease or condition refer to executing a protocol that may include a bone repair procedure, where the bone implant and/or one or more drugs are administered to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The term "bone," as used herein, refers to bone that is cortical, cancellous or cortico-cancellous of autogenous, allogenic, xenogenic, or transgenic origin.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "osteoconductive," as used herein, refers to the ability of a non-osteoinductive substance to serve as a suitable template or substance along which bone may grow.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

In other instances, osteoinduction is considered to occur through cellular recruitment and induction of the recruited cells to an osteogenic phenotype. Osteoinductivity score refers to a score ranging from 0 to 4 as determined according to the method of Edwards et al. (1998) or an equivalent calibrated test. In the method of Edwards et al., a score of "0" represents no new bone formation; "1" represents 1%-25% of implant involved in new bone formation; "2" represents 26-50% of implant involved in new bone formation; "3" represents 51%-75% of implant involved in new bone formation; and "4" represents >75% of implant involved in new bone formation. In most instances, the score is assessed 28 days after implantation. However, the osteoinductivity score may be obtained at earlier time points such as 7, 14, or 21 days following implantation. In these instances it may be desirable to include a normal DBM control such as DBM powder without a carrier, and if possible, a positive control such as BMP. Occasionally, osteoinductivity may also be scored at later time points such as 40, 60, or even 100 days following implantation. Percentage of osteoinductivity refers to an osteoinductivity score at a given time point expressed as a percentage of activity, of a specified reference score. Osteoinductivity may be assessed in an athymic rat or in a human. Generally, as discussed herein, an osteoinductive score is assessed based on osteoinductivity in an athymic rat.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

The term "osteoimplant," as used herein, refers to any bone-derived implant prepared in accordance with the embodiments of this disclosure and, therefore, is intended to include expressions such as bone membrane or bone graft. Osteoimplant is used herein in its broadest sense and is not intended to be limited to any particular shapes, sizes, configurations, compositions, or applications. Osteoimplant refers to any device or material for implantation that aids or augments bone formation or healing. Osteoimplants are often applied at a bone defect site or bone cavity, for example, one resulting from injury, defect brought about during the course of surgery, infection, malignancy, inflammation, or developmental malformation. Osteoimplants can be used in a variety of orthopedic, neurosurgical, dental, and oral and maxillofacial surgical procedures such as the repair of simple and compound fractures and non-unions, external, and internal fixations, joint reconstructions such as arthrodesis, general arthroplasty, deficit filling, disectomy, laminectomy, anterior cervical and thoracic operations, or spinal fusions.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "demineralized," as used herein, refers to any material generated by removing mineral material from tissue, e.g., bone tissue. In certain embodiments, the demineralized compositions described herein include preparations containing less than 5%, 4%, 3%, 2% or 1% calcium by weight. Partially demineralized bone (e.g., preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," and "fully demineralized." In some embodiments, part or the entire surface of the bone can be demineralized. For example, part or the entire surface of the allograft can be demineralized to a depth of from about 100 to about 5000 microns, or about 150 microns to about 1000 microns. In some embodiments, part or all of the surface of the allograft can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the outer surface of the intervertebral implant can be masked with an acid resistant coating or otherwise treated to selectively demineralize unmasked portions of the outer surface of the intervertebral implant so that the surface demineralization is at discrete positions on the implant.

The term "demineralized bone matrix," (DBM) as used herein, refers to any material generated by removing mineral material from bone tissue. In some embodiments, the DBM compositions as used herein include preparations containing less than 5%, 4%, 3%, 2% or 1% calcium by weight. In other embodiments, the DBM compositions comprise partially demineralized bone (e.g., preparations with greater than 5% calcium by weight but containing less than 100% of the original starting amount of calcium) are also considered within the scope of the current application. DBM preparations have been used for many years in orthopedic medicine to promote the formation of bone. For example, DBM has found use in the repair of fractures, in the fusion of vertebrae, in joint replacement surgery, and in treating bone destruction due to underlying disease such as a bone tumor. DBM has been shown to promote bone formation in vivo by osteoconductive and osteoinductive processes. The osteoinductive effect of implanted DBM compositions results from the presence of active growth factors present on the isolated collagen-based matrix. These factors include members of the TGF-R, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

The term "superficially demineralized," as used herein, refers to bone-derived elements possessing at least about 90, 91, 92, 93, 94, 95, 96, 97, 98 or 99 weight percent of their original inorganic mineral content. The expression "partially demineralized" as used herein refers to bone-derived elements possessing from about 8 to about 90 weight percent of their original inorganic mineral content. In some embodiments, partially demineralized refers to bone-derived elements possessing from about 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88 to about 90 weight percent of their original inorganic mineral content. The expression "fully demineralized" as used herein refers to bone containing less than 8%, 7%, 6%, 5%, 4%, 3%, 2%, or 1% of its original mineral context.

The terms "pulverized bone", "powdered bone" or "bone powder" as used herein, refers to bone particles of a wide range of average particle size ranging from relatively fine powders to coarse grains and even larger chips.

The allograft can comprise bone fibers. Fibers include bone elements whose average length to average thickness ratio or aspect ratio of the fiber is from about 50:1 to about 1000:1. In overall appearance the fibrous bone elements can be described as elongated bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the elongated bone fibers are of irregular shapes including, for example, linear, serpentine or curved shapes. The elongated bone fibers are demineralized, in some embodiments, however, some of the original mineral content may be retained when desirable for a particular embodiment. The fibers when wet relax because they are porous, as they dry, they become more entangled and can be mechanically entangled to form a coherent mass as the fibers interconnect. In some embodiments, even when the fibers are wet, they are still cohesive.

"Non-fibrous," as used herein, refers to elements that have an average width substantially smaller than the average thickness of the fibrous bone element or aspect ratio of less than from about 50:1 to about 1000:1. For example, allograft bone fibers will have a fiber shape, while the non-fibrous material will not have a fiber shape but will have a shape such as, for example, triangular prism, sphere, cube, cylinder, square, triangle, particle, powder, and other regular or irregular shapes.

"Pressed bone fibers," as used herein, refer to bone fibers formed by applying pressure to bone stock. The bone utilized as the starting, or stock, material may range in size from relatively small pieces of bone to bone of such dimensions as to be recognizable as to its anatomical origin. The bone may be substantially fully demineralized, surface demineralized, partially demineralized, or nondemineralized. In general, the pieces or sections of whole bone stock can range from about 1 to about 400 mm, from about 5 to about 100 mm, in median length, from about 0.5 to about 20 mm, or from about 2 to about 10 mm, in median thickness and from about 1 to about 20 mm, or from about 2 to about 10 mm, in median width. Forming bone fibers by pressing results in intact bone fibers of longer length than other methods of producing the elongate bone fibers retaining more of the native collagen structure. The bone fibers may be made via a cartridge mill.

"High porosity," as used herein refers to having a pore structure that is conducive to cell ingrowth, and the ability to promote cell adhesion, proliferation and differentiation.

"Resorbable," as used herein, refers to a material that exhibits chemical dissolution when placed in a mammalian body.

"Bioactive agent" or "bioactive compound," as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD peptide.

"Coherent mass," as used herein, refers to a plurality of bone fibers, in some embodiments, bound to one another by mechanical entanglement of the fibers. The cohesive mass may be in a variety of shapes and sizes, and is implantable into a surgical location. The cohesive mass comprises at least two bone fibers, in some aspects, curled or partially curled bone fibers that entangle with one another to maintain a connection without the use of a binding agent or carrier. In some embodiments, the fibers when wet relax because they are porous, as they dry, they become more entangled and form a coherent mass as the fibers interconnect.

The term "implantable" as utilized herein refers to a biocompatible device (e.g., implant) retaining potential for successful placement within a mammal. The expression "implantable device" and expressions of the like import as utilized herein refers to an object implantable through surgery, injection, or other suitable means whose primary function is achieved either through its physical presence or mechanical properties. An example of the implantable device is the osteoimplant.

Localized delivery includes delivery where one or more implants are deposited within a tissue, for example, a bone cavity, or in close proximity (within about 0.1 cm, or in some aspects, within about 10 cm, for example) thereto.

Particle refers to pieces of a substance of all shapes, sizes, thickness and configuration such as fibers, threads, narrow strips, thin sheets, clips, shards, etc., that possess regular, irregular or random geometries. It should be understood that some variation in dimension will occur in the production of the particles and particles demonstrating such variability in dimensions are within the scope of the present application. For example, the mineral particles (e.g., ceramic) can be from about 0.5 mm to about 3.5 mm. In some embodiments, the mineral particles can be from about 0.2 mm to about 1.6 mm.

In some embodiments, the coherent mass of mechanically entangled demineralized bone fibers forms a matrix. The "matrix" of the present application is utilized as a scaffold for bone and/or cartilage repair, regeneration, and/or augmentation. Typically, the matrix provides a 3-D matrix of interconnecting pores, which acts as a scaffold for cell migration. The morphology of the matrix guides cell migration and cells are able to migrate into or over the matrix, respectively. The cells then are able to proliferate and synthesize new tissue and form bone and/or cartilage. In some embodiments, the matrix is resorbable.

In some embodiments, the matrix can be malleable, cohesive, flowable and/or can be shaped into any shape. The term "malleable" includes that the matrix is capable of being converted from a first shape to a second shape by the application of pressure.

The term "cohesive" as used herein means that the mechanically entangled demineralized bone fibers tend to remain a singular, connected mass upon movement, including the exhibition of the ability to elongate substantially without breaking upon stretching.

The term "moldable" includes that the matrix can be shaped by hand or machine or injected in the target tissue site (e.g., bone defect, fracture, or void) in to a wide variety of configurations. In some embodiments, the matrix can be formed into sheets, blocks, rings, struts, plates, disks, cones, pins, screws, tubes, teeth, bones, portion of bone, wedges, cylinders, threaded cylinders, or the like, as well as more complex geometric configurations.

Reference will now be made in detail to certain embodiments of the disclosure. The disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Mesh Material

Suitable mesh materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, polyhydroxyalkanoates (polyhydroxybutyrates and polyhydroxyvalerates and copolymers), polysaccharides, polyhydroxyalkanoates polyglycolide-co-caprolactone, polyethylene oxide, polypropylene oxide, polyglycolide-co-trimethylene carbonate, poly(lactic-co-glycolic acid), and others. See Chen and Wu, "The Application of Tissue Engineering Materials," Biomaterials, 2005, 26(33): p. 6565-78, herein incorporated by reference in its entirety. Other suitable materials include carbon fiber, metal fiber, polyertheretherketones, non-resorbable polyurethanes, polyethers of all types, polyethylene terephthalate, polyethylene, polypropylene, Teflon, and various other meshes. In other embodiments, the mesh may comprise non-woven material such as spun cocoon or shape memory materials having a coil shape or shape memory alloys.

In some embodiments, woven material and braided material can be included in the mesh that can be used in this application. For example, U.S. Pat. No. 8,740,987, herein incorporated by reference in its entirety discloses tissue-derived mesh for orthopedic regeneration. In other embodiments, the mesh can include non-woven materials, shape memory material, porous materials and non-porous materials. In yet other embodiments, outer particles may be used to contain inner particles, particles may be attached to threads of material, and/or porosity may be added to mesh fibers.

In some embodiments, mesh fibers may be treated to impart porosity to the fibers. This may be done, for example, to PLA, PLGA, PGA, and other fibers. The implantable mesh is porous having pores from about 100 to about 200 μm.

One suitable method for treating the mesh fibers comprises supercritical carbon dioxide treatment to partially solubilize the particles. This treatment may further be carried out for viral inactivation. Another suitable method for treating the mesh fibers comprises explosive decompression. Explosive decompression generates porosity and leads to controlled permeability. The mesh material further may be loaded with cells, growth factors, or bioactive agents.

In further embodiments, fibers of a mesh material may be treated by having particles adhered thereto. The particles may be, for example, bone particles. Thus, in one embodiment, the mesh may comprise a plurality of threads formed into a fabric. The threads may have particles adhered thereto. For example, the threads may have particles strung on the thread. In an alternative embodiment, the mesh may be formed of a material and the material may be coated with particles.

In yet other embodiments, the mesh may comprise a non-porous material, which may be permeable. A non-porous material may be used for later (or delayed) delivery of a substance provided therein. Such substance may comprise, for example, cells, growth factors, or bone morphogenetic proteins. Accordingly, in one embodiment, a delivery system for delayed delivery of cells, growth factors, or bone morphogenetic proteins is provided comprising a non-porous mesh.

In particular, in various embodiments, the mesh may comprise a bioerodible, a bioabsorbable, and/or a biodegradable biopolymer that may provide immediate release, or sustained release of an additive, in some aspects, a bioactive agent. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. Useful biodegradable synthetic polymers include, for example, polylactic acid, polyglycolide, polylactic polyglycolic acid copolymers (PLGA), polycaprolactone (PCL), poly(dioxanone), poly (trimethylene carbonate) copolymers, polyglyconate, poly (propylene fumarate), poly(ethylene terephthalate), poly (butylene terephthalate), polyethylene glycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, that can be polymerized from the monomers related to previously-listed homo- and copolymers. Useful materials to be incorporated into the mesh may include, for example, natural polymers such as proteins and polypeptides, glycosaminoglycans, proteoglycans, elastin, hyaluronic acid, dermatan sulfate, gelatin, or mixtures or composites thereof. Synthetic polymers may also be incorporated into the bone graft composites.

As persons of ordinary skill are aware, mPEG and/or PEG may be used as a plasticizer for PLGA, but other polymers/excipients may be used to achieve the same effect. mPEG imparts malleability to the resulting formulations.

In some embodiments, these biopolymers may also be coated on the mesh to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the medical device. In some embodiments, the range of the coating on the mesh ranges from about 5 microns to about 250 microns or 5 microns to about 200 microns to delay release from the mesh. In various embodiments, the medical device comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

Generally, the mesh may be formed as a sheet. In some embodiments, the material may be a textile type material. Thus, for example, the mesh may be formed using a textile approach such as weaving, rug making or knitting. Such formation may be by a mechanical or industrial method. In another embodiment, a substantially solid sheet may be formed and may be treated to assume a configuration penetrable by cells, fluids, and proteins. For example, the sheet may be perforated, may be expanded to create openings, or otherwise make it penetrable by cells, fluids and proteins.

In one embodiment, elongated bone-derived particles or fragments of small intestinal submucosa may be combined longitudinally into three small bundles, each having, for example, from about 1 to about 3 tissue particles. The three bundles may then be braided. Various methods of braiding and types of braids any of which may be useful in producing the mesh useful in this application. The ends of the braided tissue-derived particles may then be glued together using a fixation agent to prevent their unraveling, or they may be held together with a biocompatible polymer or metal band.

In an alternative embodiment, bone-derived particles are combined with a solvent to form a material that can be used to generate threads for weaving into a mesh. Exemplary solvents include water, lower alkanols, ketones, and ethers and mixtures of any of these or other materials. The material may then be extruded at an appropriate temperature and pressure to create a thread. Threads may also be produced by spinning, drawing, rolling, solvent-extruding, cutting or laser cutting from a sheet or bar stock. The material may alternatively be cast or molded into a solid sheet or bar stock and then cut into thin threads. These may be used immediately or woven into a mesh. Alternatively, or in addition, they may be spliced, wrapped, plied, cabled, braided, woven, or some combination of these. The material may be shaped by thermal or chemical bonding, or both. In one embodiment, a portion of the solvent is removed from the material before extrusion.

Alternatively or in addition, the material may be cast as a slurry, extruded, or molded. A variety of materials processing methods will be well known to those skilled in the art. For example, the material may be solvent cast using a press such as a Carver press to spread the material into a film. Solvent evaporation will yield a porous film. Alternatively, the material may be compression molded into a film. The mesh size or porosity of the film will depend on the thickness of the film and the viscosity of the precursor and can be easily manipulated by one skilled in the art. Where elongated particles are used in an extruded aggregate, they will tend to be aligned roughly parallel to one another.

In an alternative embodiment, a thread of a biocompatible natural or synthetic material, for example, polylactide or collagen, may be coated with tissue-derived or other elements, for example, by dubbing. For example, a polymer fiber may be coated with an adhesive, for example, lecithin, and bone particles or other osteoconductive or osteoinductive fibrils allowed to adhere to the thread. The thread may then be twisted on itself or with a second or a plurality of similarly treated threads. Alternatively, or in addition, the threads may be braided. The adhesive may be a lipid that is waxy at room temperature, for example, a di- or tri-glyceride that is solid at room temperature. Alternatively, or in addition, the adhesive may be a phosphocholine or phosphatidylcholine. In some embodiments, the adhesive is a material that binds both the thread and the material that is used to coat the thread (e.g., bone particles) but that does not degrade either. Non-aqueous adhesives may improve the stability of the final aggregate as compared to aqueous adhesives.

Suitable fibers may be formed utilizing well known techniques, including braiding, plying, knitting, weaving, felting, that are applied to processing natural fibers, for example, cotton, silk, and synthetic fibers made from synthetic bioabsorbable polymers, such as poly(glycolide) and poly(lactic acid), nylon, cellulose acetate. In some embodiments, collagen thread is wound onto cylindrical stainless steel spools. The spools are then mounted onto the braiding carousel, and the collagen thread is then assembled in accordance with the instructions provided with the braiding machine. In one particular run, a braid was prepared of four collagen threads, which consisted of two threads of non-crosslinked collagen and two threads of crosslinked collagen. One skilled in the art will recognize that these techniques may be applied to the other fibrous materials described herein.

Fibers and more evenly dimensioned particles may also be plied into yarns using the same methods and same machinery known to those skilled in the art in plying threads made out of other material, such as cotton or polyester. Four collagen threads were twisted together. Three of the resultant 4-ply strands were then twisted together in the opposite direction, and then 5 of the resultant 12 ply strands were twisted in the opposite direction.

Elongated materials including multistranded materials, for example, braids, plied yarns or cables, may be knitted into tubular or flat fabrics by using techniques known to those skilled in the art of producing fabrics manufactured from other types of threads. Various biologically active substances can be incorporated in, or associated with, the braided, knitted, or woven materials. Particles and fibers and materials of these (including multistranded materials) may alternatively or additionally be assembled into a material by non-woven methods such as laying, needle-punching, and hooking (as for a rug). For example, a thread may be attached to another thread or a pressed film.

Regardless of the assembly method, the material shape, mesh size, cable thickness, and other structural characteristics, such as architecture, may be customized for the desired application. For example, where a two dimensional aggregate is used to retain a thixotropic material within a gap, a tight weave is used, in some aspects, to prevent leakage. To optimize cell or fluid migration through the mesh, the pore size may be optimized for the viscosity and surface tension of the fluid or the size of the cells. For example, pore sizes on the order of approximately from about 100 µm to about 200 µm may be used if cells are to migrate through the implantable mesh. Mesh size may be controlled by physically weaving strands of the material by controlling the ratio of solvent to solids in a precursor material.

Cells may be seeded onto the mesh, or contained within it. In one embodiment, cells may be encapsulated in a matrix such as alginate or collagen gel and the capsules placed on the material. Seeded materials generally do not need to be incubated for long periods of time in solutions that could partially dissolve the binding agent. Instead, the capsules may be placed on the mesh shortly before implantation. In another embodiment, cells are simply mixed with a gel which is then combined with the mesh. Alternatively, the mesh may be cultured with cells before implantation. In one embodiment, thicker materials are used for culturing to increase mechanical integrity during implantation. Any class of cells, including connective tissue cells, organ cells, muscle cells, nerve cells, and stem cells, may be seeded onto the implant. In an exemplary embodiment, connective tissue cells such as osteoblasts, osteoclasts, fibroblasts, tenocytes, chondrocytes, and ligament cells and partially differentiated stem cells such as mesenchymal stem cells and bone marrow stromal cells are employed.

Bone Material

DBM compositions and methods that allow osteogenesis, osteoinduction and/or osteoconduction are provided. DBM compositions and methods are provided that allow osteogenesis, osteoinduction and/or osteoconduction. The DBM compositions and methods provided, in some embodiments, are made from bone material that does not contain or require a carrier in order to stay in place during a surgical procedure and are also irrigation resistant. DBM compositions, devices and methods that easily allow hydration of the demineralized bone matrix are also provided.

Bone can be milled into fibers, shavings, sheets, prior to or after demineralization. Demineralized bone also naturally contains collagen fibers of various lengths depending on the milling/cutting process.

In some embodiments, demineralized bone fibers can be milled and formed into mats with random fiber orientation. Subsequently, in other aspects, the demineralized bone fiber mats can be bonded together by applying moisture, heat and pressure created by pressure rollers so that the demineralized bone fibers form a nonwoven sheet of matted fibers.

In other embodiments, the demineralized bone fibers can be further mechanically entangled by additional mechanical means, such as needle punching, spun-lace entanglement or by applying ultrasonic waves. In some embodiments, felting needles can engage demineralized bone fibers and mechanically entangle them into a mesh sheet to permanently transport bundles of fibers into the mesh sheet to create a coherent fibrous structure of demineralized bone fibers mechanically entangled into an implantable mesh.

In various embodiments, the felting needles can be forked or barbed and are used to hook the fibers to perform a fiber entanglement function. There are many variations in needle design, barb placement, barb angle and barb shape. FIG. 1 illustrates two embodiments of barbed needle design. Each needle 10 and 12 include a crank 14, a shank 16, in one aspect with an intermediate blade 18, a tip blade 24 and a point 26. Each needle can have the same or a different barb placement. For example, needle 10 has barbs 20 at an angle that is different and opposite in direction to the angle of the barbs 22 of needle 12.

Figure 2:
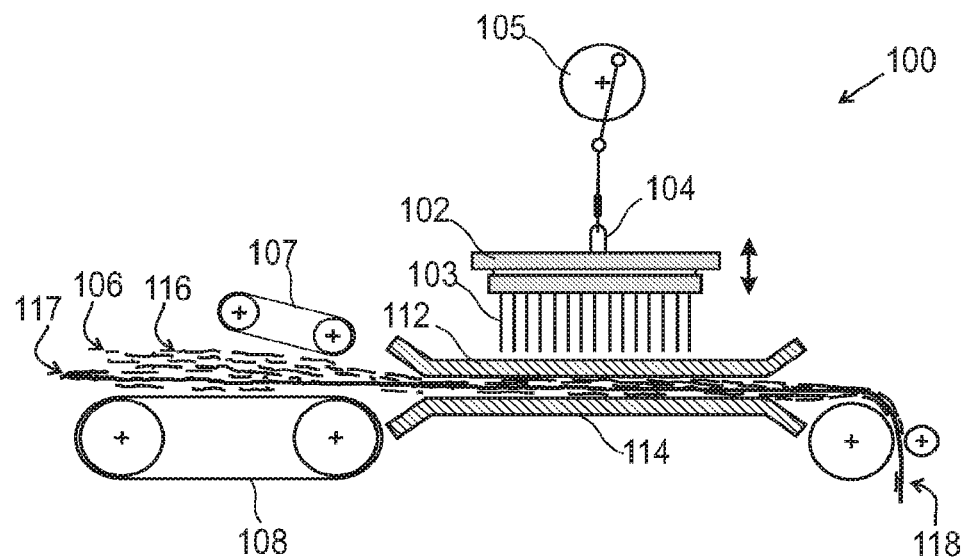
FIG. 2 depicts a schematic of a needle punching process.

FIG. 2 is a simplified schematic of a process of forming an implantable mesh comprising, consisting essentially of, or consisting of demineralized bone fibers mechanically entangled into a biodegradable or non-biodegradable mesh by utilizing a conventional needle punching or felting apparatus 100. Generally, a needle punching or felting apparatus includes a needle board 102 fastened to a needle beam or another device 104 which is adapted to move up and down in a reciprocating motion as driven by a main drive 105. The needle board 102 comprises a multitude of felting or barb needles 103. Barb needles 103 of needle beam or device 104 penetrate a mesh 117 and mechanically entangle demineralized bone fibers 116 into mesh 117. Demineralized bone fibers 106 from input device 107 pass through a batt compression process 108, followed, in some aspects by pressure applied by calendar rolls (not shown) and pass between a perforated stripper plate 112 to a bed plate 114 where the film of demineralized bone fibers 116 is further pressed and/or needle punched into mesh 117 to form an implantable mesh having demineralized bone fibers mechanically entangled therein 118. The resulting DBMs are thus reinforced by the mesh into which they are mechanically entangled and can be used as surgical wraps which can be sutured without tearing. In a nonwoven fabric of demineralized bone fibers, the coherent mass of demineralized bone fibers is held together by mechanical entanglement in a random web or mat.

Figure 3:
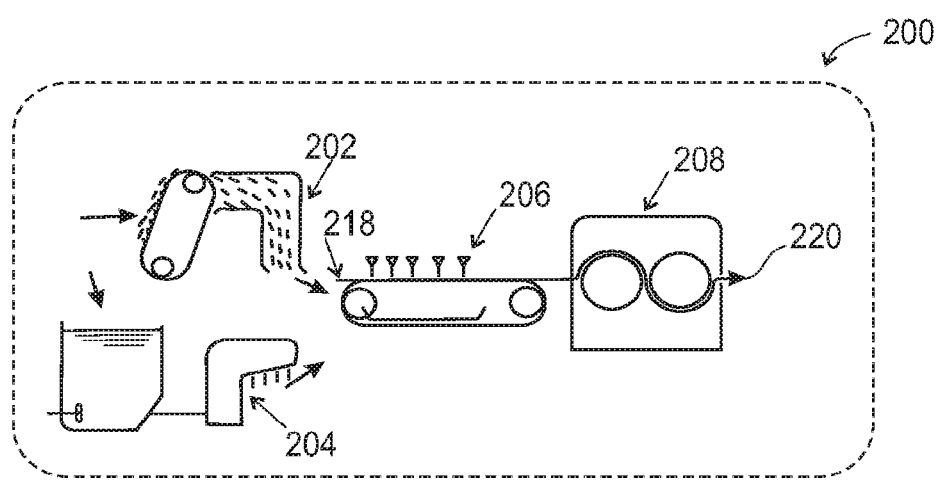
FIG. 3 depicts a schematic of a spunlaced or hydroentanglement process.

FIG. 3 illustrates another embodiment of a process for making an implantable mesh containing demineralized bone fibers mechanically entangled therein. FIG. 3 is a simplified schematic of a spun lace or entanglement process 200 of making an implantable mesh 220 containing demineralized bone fibers 202 mechanically entangled into mesh 218. In this process, a bale of demineralized bone fibers either dry 202 or wet 204 becomes entangled into mesh 218 by using high velocity jets of water or air 206 to form the implantable mesh 220. In some aspects, the implantable mesh 220 can be subjected to a drying process 208 prior to exiting the spun lace process. The water pressure of the water jet injectors 206 generally increases from the first to the last water jet injectors. In some embodiments, pressures as high as 2200 psi can be used to direct the water jets onto the web of demineralized bone fibers.

Figure 4A:
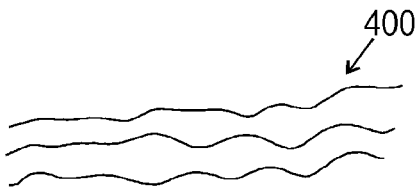
FIG. 4A depicts a side view of DBM fibers.
Figure 4B:
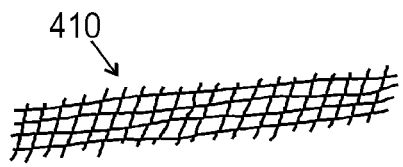
FIG. 4B illustrates a side view of reinforcement mesh.
Figure 4C:
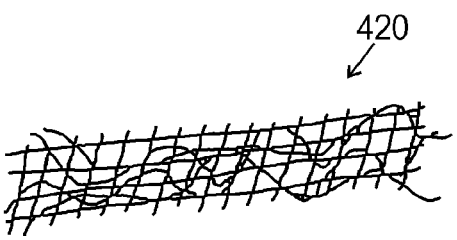
FIG. 4C is a side view of an implant mesh resulting from mechanically entangling the DBM fibers of FIG. 4A into the Mesh of FIG. 4B.

FIG. 4A is a side view of DBM fibers 400. FIG. 4B is a side view of bioresorbable or permanent mesh 410. FIG. 4C is a side view of the implantable mesh 420 resulting from mechanically entangling the DBM fibers 400 of FIG. 4A with the mesh 410 of FIG. 4B. The bone fibers 400 are mechanically entangled into the mesh along the mesh's longitudinal axis and the bone fibers can be continuous with the mesh as shown in FIG. 4C. The bone fibers can extend outside of the mesh as shown in FIG. 4C. In some embodiments, the bone fiber of the mesh can alternate with the polymer mesh. Therefore, the mesh can comprise a strand of polymer and then alternate with a strand of fiber, then a strand of polymer, and then a strand of fiber to have alternating strands that comprise the mesh.

In some embodiments, the mesh comprises the same or more polymer than bone fiber. In some embodiments, the mesh comprises a polymer that makes up from about 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, 60%, 65%, 70%, 75%, 80%, 85%, to about 90% w/w of the mesh.

In some embodiments, the mesh comprises a bone fibers that makes up from about 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5, to about 60% w/w of the mesh.

In some embodiments the biodegradable fibers of the mesh can be entangled with the demineralized bone fibers to form a plurality of layers in the implantable mesh (not shown). For example, in other aspects, bone fibers can be mechanically entangled with non-bone fibers and further mechanically entangled with the biodegradable mesh.

Figure 5A:
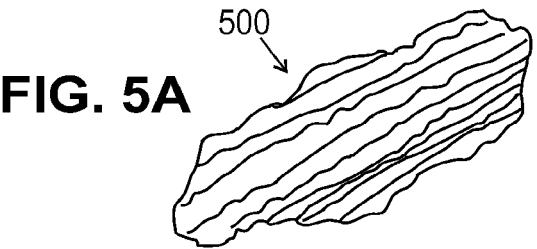
FIG. 5A depicts an example of DBM sheets/shavings containing natural collagen fibers.
Figure 5B:
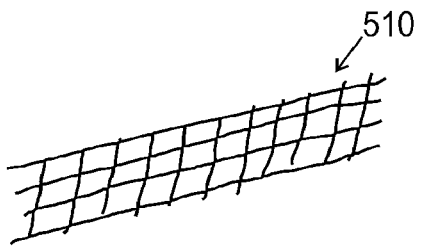
FIG. 5B depicts a mesh that can be used to reinforce the DBM sheets/shavings of FIG. 5A.
Figure 5C:
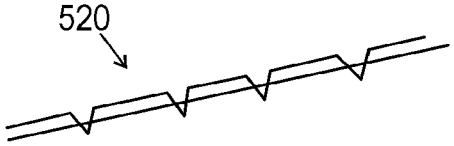
FIG. 5C illustrates an implant mesh resulting from mechanically entangling the DBM sheets/shavings of FIG. 5A into the mesh of FIG. 5B.

In some embodiments, DBM fibers can be milled, for example, cartridge milled. The acid extraction process can be conducted so as to leave collagen, noncollagenous proteins, and growth factors together in a solid fiber. FIG. 5A illustrates an example of DBM sheets and/or shavings 500 containing natural collagen fibers. FIG. 5B illustrates an example of a mesh 510 that could be used to reinforce the DBM sheets and/or shavings 500 containing collagen fibers of FIG. 5A. When the DBM sheets/shavings 500 are mechanically entangled with mesh 510, implantable mesh 520 of FIG. 5C obtains. In some embodiments the biodegradable fibers of the mesh can be entangled with the DBM sheets and/or shaving containing collagen fibers to form a plurality of layers in the implantable mesh (not shown).

By mechanically entangling the DBM fibers, sheets or shaving into a mesh, the DBM fibers are reinforced and can stay together more than from 10%, 15%, 20%, 25%, 30%, 35%, 40%, 45%, 50%, 55%, 60%, 65%, 70%, 75%, 80%, 85%, 90%, 95%, 99% to 100% than if they were not mechanically entangled, even after wetting the implantable mesh containing the mechanically entangled DBMs.

In some embodiments, the implantable mesh containing the mechanically entangled DBMs does not have a carrier or binding agent. Thus, after entanglement the implantable mesh is 99% or more free of a carrier or binding agent, yet still holds together. Examples of suitable binding agents or carrier that optionally can be included after the implantable mesh is formed include, but are not limited to, glycerol, polyglycerol, polyhydroxy compound, for example, such classes of compounds as the acyclic polyhydric alcohols, non-reducing sugars, sugar alcohols, sugar acids, monosaccarides, disaccharides, water-soluble or water dispersible oligosaccharides, polysaccharides and known derivatives of the foregoing. Specific polyhydroxy compounds include, 1,2-propanediol, glycerol, 1,4-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic® and Emkalyx®; polyoxyethylene-polyoxypropylene block copolymer, for example, of the type known and commercially available under the trade name Poloxamer®; alkylphenol-hydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing.

The carrier or binding agent optionally used may further comprise a hydrogel such as hyaluronic acid, dextran, Pluronic® block copolymers of polyethylene oxide and polypropylene, and others. Suitable polyhodroxy compounds include such classes of compounds as acyclic polyhydric alcohols, non-reducing sugars, sugar alcohols, sugar acids, monosaccharides, disaccharides, water-soluble or water dispersible oligosaccharides, polysaccharides and known derivatives of the foregoing. An example carrier comprises glyceryl monolaurate dissolved in glycerol or a 4:1 to 1:4 weight mixtures of glycerol and propylene glycol. Settable materials may be used, and they may set up either in situ, or prior to implantation. Optionally, xenogenic bone powder carriers also may be treated with proteases such as trypsin. Xenogenic carriers may be treated with one or more fibril modifying agents to increase the intraparticle intrusion volume (porosity) and surface area. Useful agents include solvents such as dichloromethane, trichloro-acetic acid, acetonitrile and acids such as trifluoroacetic acid and hydrogen fluoride. The choice of carrier may depend on the desired characteristics of the composition. In some embodiments, a lubricant, such as water, glycerol, or polyethylene glycol may be added.

Compositions and methods are provided for an implantable mesh containing mechanically entangled demineralized bone fibers for hydration with a liquid, the implantable mesh having no carrier disposed in or on it. After the demineralized bone fibers are mechanically entangled into the mesh, in some aspects, the resulting implantable mesh can be lyophilized. In some embodiments, the demineralized bone fibers are cartridge milled and have a ribbon-like shape and increased surface area. In some embodiments, after the demineralized bone fibers are cartridge milled, they can be subjected to process of mechanical entanglement as discussed above and the resulting implantable mesh can be subsequently lyophilized.

In some embodiments, the milled and lyophilized mechanically entangled demineralized bone fibers comprise autograft or allograft bone. In some embodiments, the bone fibers have a diameter from about 100 µm to about 2 mm. In some embodiments, the bone fibers have a length from about 0.5 mm to about 50 mm. In some embodiments, the bone fibers have an average length from about 0.5 cm to about 10 cm. In some embodiments, the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In some embodiments, the liquid for hydration of the fibers comprises blood, water, saline or a combination thereof. In some embodiments, the liquid for hydration of the fibers is mixed with the implantable mesh having milled and demineralized bone fibers mechanically entangled therein to form moldable lyophilized demineralized bone fiber implantable mesh.

In some embodiments, the milled and lyophilized demineralized bone fibers that are mechanically entangled into the mesh do not contain a carrier. In some aspects, the demineralized bone fibers comprise cartridge milled fibers having a curled portion. In some embodiments, the implantable mesh of milled and lyophilized demineralized bone fibers comprises autograft or allograft bone. In some embodiments, the bone fibers have a diameter from about 100 µm to about 2 mm. In some embodiments, the bone fibers have a length from about 0.5 mm to about 50 mm. In some embodiments, the bone fibers have an average length from about 0.5 cm to about 10 cm. In some embodiments, the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In some embodiments, the liquid for hydration of the fibers comprises physiologically acceptable water, physiological saline, sodium chloride, dextrose, Lactated Ringer's solution, phosphate buffered saline (PBS), blood, bone marrow aspirate, bone marrow fractions or a combination thereof in an amount sufficient to render the implantable osteogenic material moldable. In some embodiments, the liquid is mixed with the lyophilized implantable mesh containing mechanically entangled demineralized bone fibers to form moldable lyophilized demineralized bone fiber.

In some embodiments, the implantable mesh comprises cortical bone, cancellous bone, cortico-cancellous bone, or mixtures thereof. In some embodiments, the bone material in the implantable mesh is obtained from autogenous bone, allogenic bone, xenogenic bone, or mixtures thereof. In some embodiments, the implantable mesh is lyophilized and shaped. In some embodiments, the shape of the lyophilized implantable mesh is a cube, square, triangle, rectangle, circle, disc or cylinder shape. In some embodiments, the shape of the implantable mesh having mechanically entangled demineralized bone fibers therein is disc or cylinder shaped and the disc or cylinder has a reservoir configured to contact a liquid. Compositions and methods are provided for an implantable bone graft comprising fibers obtained from allograft bone, the fibers comprising hooking portions configured to entangle with a biodegradable or permanent mesh to form an implantable mesh, wherein the composition does not include a binding agent.

Typically, when bone is processed into particles or fibers, it is statically charged and not coherent or adherent. The processed bone is normally contained within an external structure (i.e., a bag or covering) or mixed with a carrier or binding agent to provide a cohesive structure. When implanted, this external structure or carrier must be removed by the patient's body, potentially impacting the osteoinductive potential of the graft.

In some embodiments, the implantable mesh described in this application contains demineralized bone fibers which are mechanically entangled by needle punching, entanglement pressure, water or air jet or sonication to form reinforced DBMs having enhanced cohesion between fibers without a requirement for additional containment, carrier or binding agents.

In some embodiments, the curled bone fibers can be further subjected to mechanical entanglement as discussed above, so that the resulting implantable mesh is like felt in consistency and can be easily shaped into desired shapes. Further, in some aspects, the milled and/or curled fiber shape is altered during the drying process, which leads to physical entanglement and surface to surface interactions between adjacent fibers. In some embodiments, the milled fibers are subjected to the mechanical entanglement processes discussed above, namely needle punching or entanglement. The entanglement/interaction of the fibers is responsible for the cohesiveness of the final implantable mesh.

The compositions of the present disclosure results are utilized in an effective bone grafting product. The bone graft material is resorbed and/or remodeled and replaced by host bone during the healing process. In some embodiments, the bone material disclosed herein includes additional additives, such as synthetic ceramics and/or bioerodible polymers, which produce high concentrations of calcium, phosphate and silicon ions that act as a nidus for de-novo bone formation, as discussed herein. As the bioerodible polymer degrades faster than the ceramic, more and more osteoinductive DBM particles are exposed. The slower resorbing ceramic may act as a solid surface for stem cells and osteoblasts to attach to and begin laying down new bone.

The implantable mesh of this disclosure has good flexibility and is compression resistant. It is also osteoinductive with the demineralized bone matrix retaining activity. These properties make an excellent bone graft substitute in that it may not break, crack, or deform when implanted in the body.

The implantable mesh may include among its mechanically entangled DBMs a combination of fibers of bone matrix from allograft bone and fibers of non-allograft bone material. The fibers of the non-allograft bone material comprise non-fibrous demineralized bone matrix particles embedded within or dispersed on the fibers of the non-allograft bone material. The ratio of fibers of demineralized bone matrix from allograft material to fibers of non-allograft material ranges from about 20:80 to about 70:30. In one embodiment, the ratio of fibers from allograft material to fibers of non-allograft material ranges from about 40:60 to about 60:40. In one embodiment, the ratio of fibers of demineralized bone matrix from allograft material to fibers of non-allograft material is about 50:50.

In some embodiments, the demineralized bone material includes particles that are non-fibrous. In some embodiments, the particles are powders, microspheres, sponges, pastes, gels, and/or granules. In one embodiment, the particles are powders.

In some embodiments, the demineralized bone material fibers comprise from about 1 to about 70 micrometers or from about 125 to about 250 micrometers. In some embodiments, the demineralized bone material fibers comprise about 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248 and/or 250 micrometers. In some embodiments, the bone fibers include a length from about 100 micrometers to about 2 mm. In some embodiments, the bone fibers have a length from about 0.5 cm to about 10 cm, about 1 cm to about 8 cm, about 3 cm to about 5 cm, about 0.5 mm to about 50 mm, about 1.0 mm to about 25 mm, or about 5 mm to about 10 mm. The fibers include a diameter of about 100 micrometers to about 2 mm.

The fibers are milled in such a way as to provide increased surface area in a compact shape and size. In some embodiments, the fibers include a curled shape such that diameter of the curled fibers is between about 50 micrometers and about 3 mm, and the diameter of the fibers in a flattened configuration is about 125 micrometers to about 5 mm. In some embodiments, the fibers include a curled shape such that diameter of the curled fibers is between about 100 micrometers and about 1 mm, and the diameter of the fibers in a flattened configuration is about 250 micrometers to about 2 mm.

In various embodiments, the fibers have an aspect ratio of length to width from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In other embodiments, the fibers have an aspect ratio of length to width of about 4:1, 17:1, or 23:1.

The composition has very low immunogenicity and good compatibility.

DBM fibers for use in the present disclosure can be obtained commercially or can be prepared by known techniques. In general, advantageous, osteoinductive DBM materials can be prepared by decalcification of cortical and/or cancellous bone fibers, often by acid extraction. The fibers can be milled, for example, cartridge milled. The acid extraction process can be conducted so as to leave collagen, noncollagenous proteins, and growth factors together in a solid fiber. Methods for preparing bioactive demineralized bone are described in U.S. Pat. Nos. 5,073,373; 5,484,601; and 5,284,655, as examples. DBM products are also available commercially, including for instance, from sources such as Regeneration Technologies, Inc. (Alachua, Fla.), The American Red Cross (Arlington, Va.), and others. Bone fibers that are solely osteoconductive can be prepared using similar techniques that have been modified or supplemented to remove or inactivate (e.g. by crosslinking or otherwise denaturing) components in the bone matrix responsible for osteoinductivity. Osteoinductive and/or osteoconductive DBM materials used in the present disclosure can be derived from human donor tissue, especially in regard to implant devices intended for use in human subjects.

In regard to the fiber content of the implantable mesh on a dry weight basis, the bone fiber material can constitute about 5% to about 100% of the compositions, about 20% to about 80%, or about 25% to about 75% by weight.

In some embodiments, the bone fibers of allograft bone have an average length to average thickness ratio or aspect ratio of the fibers from about 50:1 to about 1000:1. In overall appearance the bone fibers can be in the form of ribbons, threads, narrow strips, and/or thin sheets. The elongated bone fibers can be substantially linear in appearance or they can be coiled to resemble springs. In some embodiments, the bone fibers have linear portions and coiled portions. In some embodiments, the bone fibers are of irregular shapes including, for example, linear, serpentine and/or curved shapes. In some embodiments, the fibers can be curled at the edges to have a substantially hemicircular cross-sections. In some embodiments, the fibers may be entirely or partially helical, circumvoluted or in the shape of a corkscrew. The elongated bone fibers can be demineralized however some of the original mineral content may be retained when desirable for a particular embodiment. The bone graft fiber may further comprise mineralized bone material.

The bone fiber sizes and shapes may be created in a number of ways, for example, through cartridge milling. One such example of a suitable cartridge mill is the Osteobiologic Milling Machine, as described in U.S. Patent Publication No. 2012/0160945, assigned to Warsaw Orthopedic, Inc. and is hereby incorporated by reference in its entirety. However, it is contemplated that the bone fibers may be alternatively milled using vices, cutters, rollers, rotating rasps or reciprocating blade mills.

Non-Bone Material Additives

In some embodiments, the bone fibers may be combined with non-bone material additives after demineralization and/or lyophilization and before implantation. For example, the bone fibers may be combined with a bioerodible polymer. The bioerodible polymer exhibits dissolution when placed in a mammalian body and may be hydrophilic (e.g., collagen, hyaluronic acid, polyethylene glycol). Synthetic polymers are suitable according to the present disclosure, as they are biocompatible and available in a range of copolymer ratios to control their degradation.

In some embodiments, hydrophobic polymers (e.g. poly (lactide-co-glycolyde), polyanhydrides) may be used. Alternatively, a combination of hydrophilic and hydrophobic polymers may be used in the bone graft composition of the disclosure.

Exemplary materials may include biopolymers and synthetic polymers such as human skin, human hair, bone, collagen, fat, thin crosslinked sheets containing fibers and/or fibers and chips, polyethylene glycol (PEG), chitosan, alginate sheets, cellulose sheets, hyaluronic acid sheet, as well as copolymer blends of poly (lactide-co-glycolide) PLGA.

Useful bioerodible polymers may have a molecular weight of from about 1,000 to about 30,000 Daltons (Da). In various embodiments, the polymer may have a molecular weight of from about 2,000 to about 10,000 Da. In some embodiments, the polymer may have a molecular weight of from about 2,000 to 4,000 Da or from about 3,000 to 4,000 Da. In some embodiments, the bioerodible polymer may have a molecular weight of 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or about 30,000 Da.

In some embodiments, the bioerodible polymer can be collagen. Collagen has excellent histocompatibility without antibody formation or graft rejection. Any suitable collagen material may be used, including known collagen materials, or collagen materials as disclosed in U.S. patent application Ser. No. 12/030,181, filed Feb. 12, 2008, hereby incorporated by reference in its entirety.

Various collagen materials can be used, alone or in combination with other materials present in the implantable mesh described in this disclosure. In some embodiments, the implantable mesh containing mechanically entangled demineralized bone fibers comprises a biodegradable polymer, such as, for example, collagen. In some embodiments, the biodegradable polymer is crosslinked. Exemplary collagens include human or non-human (bovine, ovine, piscine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collage type XX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof. In various embodiments, the collagen may be crosslinked.

Insoluble collagen material for use in the disclosure can be derived from natural tissue sources, (e.g. xenogenic, allogenic, or autogenic relative to the recipient human or other patient) or recombinantly prepared. Collagens can be subclassified into several different types depending upon their amino acid sequence, carbohydrate content and the presence or absence of disulfide crosslinks. Types I and III collagen are two of the most common subtypes of collagen and may be used in the present disclosure. Type I collagen is present in skin, tendon and bone, whereas Type III collagen is found primarily in skin. The collagen used in compositions of the disclosure can be obtained from skin, bone, tendon, or cartilage and purified by methods well known in the art and industry. Alternatively, the collagen can be purchased from commercial sources.

The collagen can be atelopeptide collagen and/or telopeptide collagen. Still further, either or both of non-fibrillar and fibrillar collagen can be used. Non-fibrillar collagen is collagen that has been solubilized and has not been reconstituted into its native fibrillar form.

Suitable collagen products are available commercially, including for example from DSM Biomedical (Exton, Pa.), which manufactures a fibrous collagen known as Semed F, from bovine tendon or hides. Collagen materials derived from bovine hide are also manufactured by Integra Life Science Holding Corporation (Plainsboro, N.J.). Naturally-derived or recombinant human collagen materials are also suitable for use in the disclosure. Illustratively, recombinant human collagen products are available from Fibrogen, Inc. (San Francisco, Calif.).

In some embodiments, the fibers can be combined with synthetic ceramics that are effective to provide a scaffold for bone growth and which are completely bioresorbable and biocompatible. The synthetic ceramics should provide high local concentrations of calcium, phosphate and silicon ions that act as a nidus for de-novo bone formation. The use of such a resorbable ceramics provides many advantages over alternative conventional materials. For instance, it eliminates the need for post-therapy surgery for removal and degrades in the human body to biocompatible, bioresorbable products.

In some embodiments, the synthetic ceramics disclosed herein may be selected from one or more materials comprising calcium phosphate ceramics or silicon ceramics. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride $(Si_3N_4)$, and biocompatible ceramics may be used. In some embodiments, the ceramic is tri-calcium phosphate or biphasic calcium phosphate and silicon ceramics. In some embodiments, the ceramic is tricalcium phosphate.

In some embodiments, the ceramics are a combination of a calcium phosphate ceramic and silicon ceramic. In some embodiments, the calcium phosphate ceramic is resorbable biphasic calcium phosphate (BCP) or resorbable tri-calcium phosphate (TCP), in some aspects, resorbable TCP.

Biphasic calcium phosphate can have a tricalcium phosphate:hydroxyapatite weight ratio of about 50:50 to about 95:5, about 70:30 to about 95:5, about 80:20 to about 90:10, or about 85:15. The mineral material can be a granular particulate having an average particle diameter between about 0.2 and 5.0 mm, between about 0.4 and 3.0 mm, or between about 0.4 and 2.0 mm.

The ceramics of the disclosure may also be oxide ceramics such as alumina ($Al_2O_3$) or zirconia ($ZrO_2$) or composite combinations of oxides and non-oxides such as silicon nitride).

In some embodiments, the composition containing the fibers may also contain other beneficial substances including, for example, preservatives, co-solvents, suspending agents, viscosity enhancing agents, ionic strength and osmolality adjusters and/or other excipients. Suitable buffering agents can also be used an include, but are not limited to, alkaline earth metal carbonates, phosphates, bicarbonates, citrates, borates, acetates, succinates, or others. Illustrative-specific buffering agents include for instance sodium phosphate, sodium citrate, sodium borate, sodium acetate, sodium bicarbonate, sodium carbonate, and sodium tromethanine (TRIS).

In some embodiments, the implantable mesh containing mechanically entangled demineralized bone fibers may be mixed with a porogen material which is later removed during manufacturing to enhance porosity of the dried implantable mesh. Suitable porogen materials may be made of any biocompatible, biodegradable substance that can be formed into a particle and that is capable of at least substantially retaining its shape during the manufacturing of the implant, but is later removed or degrades or dissolves when placed in contact with an aqueous solution, or other liquid. The porogens, in some embodiments, may be inorganic or organic, for example, they may be made from gelatin, an organic polymer (e.g., polyvinyl alcohol), polyurethanes, polyorthoesters, PLA, PGA, and PLGA copolymers, a saccharide, a calcium salt, sodium chloride, calcium phosphate or mixtures thereof. Porogen particles may be about 100 to about 500 microns.

In one embodiment, all porogen particles of a given morphology can have at least one average axial, transverse, or lateral dimension that is about 100 to about 500 microns. In some embodiments, all porogen particles used can independently have at least one axial, transverse, or lateral dimension that is about 100 to about 500 microns. In some embodiments, all porogen particles used can collectively have at least one average axial, transverse, or lateral dimension that is about 100 to about 500 microns. In some embodiments, at least one dimension of the porogen particles can be about 100 microns or more, or about 120 microns or more, or about 140 microns or more. In some embodiments, at least one dimension of the porogen particles can be about 500 microns or less, about 425 microns or less, about 350 microns or less, about 300 microns or less, or about 250 microns or less. In some embodiments, the porogen particles can have at least one dimension that is about 120 to about 400 microns.

In some embodiments the implantable mesh containing demineralized bone fibers mechanically entangled therein could contain single or multiple concentrations of size controlled fibers to affect its consistency and affect the handling of the implantable mesh after hydration.

In some instances multiple implantable meshes might be packaged together to improve their handling prior to and after hydration. In other instances the implantable meshes may be hydrated with a polar or non-polar solutions and/or salt solutions prior to drying to enhance later rehydration.

One of more biologically active ingredients may be added to the resulting composition (for example, lyophilized bone fibers). These active ingredients may or may not be related to the bone repair capabilities of the composition. Suitable active ingredients hemostatic agents, bone morphogenic proteins (BMPs), genes, growth differentiation factors (GDFs), or other non-collagenic proteins such as TGF-β, PDGF, ostropontin, osteonectin, cytokines, and the like.

In one embodiment, the implantable mesh containing mechanically entangled demineralized bone fibers therein can include at least one BMP, which are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, the implantable mesh containing demineralized bone fibers mechanically entangled therein can also include one or more Growth Differentiation Factors ("GDFs") disposed in it. Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BCO30959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

The implantable mesh containing demineralized bone fibers mechanically entangled therein can also include: GDF-11 polynucleotides or polypeptides corresponding to GenBank Accession Numbers AF100907, NP005802 or 095390, as well as mature GDF-11 polypeptides or polynucleotides encoding the same; GDF-15 polynucleotides or polypeptides corresponding to GenBank Accession Numbers BC008962, BC000529, AAH00529, or NP004855, as well as mature GDF-15 polypeptides or polynucleotides encoding the same.

In some embodiments, the implantable mesh having demineralized bone fibers mechanically entangled therein contains other bioactive agents which can be delivered with it. In certain embodiments, the bioactive agent is a drug. These bioactive agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergic, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, antiarthritics, and diagnostic agents. A more complete listing of bioactive agents and specific drugs suitable for use in the present disclosure may be found in "The Merck Index: An Encyclopedia of Chemicals, Drugs, and Biologicals," Edited by Susan Budavari, et al.; and the United States Pharmacopoeia/National Formulary XXXVII/XXXII, published by the United States Pharmacopeial Convention, Inc., Rockville, Md., 2013, each of which is incorporated herein by reference.

Bioactive agents may also be provided by incorporation into the implantable mesh having mechanically entangled demineralized bone fibers therein. Bioactive agents such as those described herein can be incorporated homogeneously or regionally into the implant material by simple admixture or otherwise. Further, they may be incorporated alone or in conjunction with another carrier form or medium such as microspheres or another microparticulate formulation. Suitable techniques for forming microparticles are well known in the art, and can be used to entrain or encapsulate bioactive agents, whereafter the microparticles can be dispersed within the bone graft composite upon or after its preparation.

It will be appreciated that the amount of additive used will vary depending upon the type of additive, the specific activity of the particular additive preparation employed, and the intended use of the composition. The desired amount is readily determinable by the user.

Any of a variety of medically and/or surgically useful substances can be incorporated in, or associated with, the allograft bone material either before, during, or after preparation of the implantable mesh containing mechanically entangled demineralized bone fibers. Thus, for example, when the non-allograft bone material is used, one or more of such substances may be introduced into the bone fibers, for example, by soaking or immersing these bone fibers in a solution or dispersion of the desired substance(s).

In some embodiments, the implantable mesh containing biodegradable fibers mechanically entangled therein can be lyophilized with one or more growth factors (e.g., BMP, GDF), drugs so that it can be released from the implantable mesh in a sustained release manner.

Bone Fiber Shapes

The present disclosure also provides methods for shaping the implantable mesh containing mechanically entangled demineralized bone fibers therein. The fibers utilized in the implantable mesh, in some aspects can be milled from bone shafts using any appropriate apparatus, such as a cartridge mill. The fibers are milled to include curled shapes having frayed portions and/or hooked portions to facilitate mechanical entanglement of the fibers. The shape of the allograft may be tailored to fit the site at which it is to be situated. For example, it may be in the shape of a morsel, a plug, a pin, a peg, a cylinder, a block, a wedge, ring, or a sheet. In some embodiments, the implantable mesh may be shaped as a wrap for wrapping around a bone defect and to contain other allograft or synthetic material into which a surgeon or another medical practitioner can safely place sutures without unraveling.

In one embodiment, the method comprises placing the implantable mesh having mechanically entangled demineralized bone fibers into a mold prior to demineralization and/or lyophilization. The bone fibers in the implantable mesh are then demineralized, sterilized and/or lyophilized to create a shaped mesh containing mechanically entangled demineralized bone fibers. The bone fibers mechanically entangled into the implantable mesh can be placed into a mold and then subjected to demineralization and/or lyophilization to make the desired shape or the bone fibers can be demineralized, mechanically entangled into the implantable mesh and/or lyophilized and then shaped by stamping or punching the desired shape. The demineralization and lyophilization steps alter the shape of the bone fibers to facilitate mechanical entanglement, as discussed herein. The bone fibers mechanically entangled into the implantable mesh do not require the use of a binding agent or carrier to form the implantable mesh.

In some embodiments, the demineralized bone fibers mechanically entangled into a mesh can be placed into molds and shaped to form a in a range of predetermined shapes and sizes according to the needs of a medical procedure. In some embodiments, the allograft may be made by injection molding, compression molding, die pressing, slip casting, laser cutting, water-jet machining, sand casting, shell mold casting, lost tissue scaffold casting, plaster-mold casting, vacuum casting, permanent-mold casting, slush casting, pressure casting, die casting, centrifugal casting, squeeze casting, rolling, forging, swaging, extrusion, shearing, spinning, or combinations thereof. For example, the implantable mesh may be rectangular, pyramidal, triangular, pentagonal, or other polygonal or irregular prismatic shapes.

Demineralization

After the bone is obtained from the donor it can be demineralized before or after it is formed into a fiber. In some embodiments, after the bone is obtained from the donor and milled into a fiber, it is processed, namely, cleaned, disinfected, and defatted using methods well known in the art. The entire bone can then be demineralized or, if desired, the bone can just be sectioned before demineralization. The entire bone or one or more of its sections is then subjected to demineralization in order to reduce the inorganic content to a low level, e.g., to contain less than about 10% by weight, in some aspects, less than about 5% by weight and in other aspects, less than about 1% by weight, residual calcium.

DBM may be prepared in any suitable manner. In one embodiment, the DBM is prepared through the acid extraction of minerals from bone. It includes the collagen matrix of the bone together with acid insoluble proteins including bone morphogenic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues. As noted, in embodiments of bone particles taken from cortical long bones, the osteoinductive potential of the bone particles when demineralized may vary based on the source of the bone particles, whether from the periosteal layer, the middle layer, or the endosteal layer.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In one demineralization procedure, the implantable mesh can be subjected to an acid demineralization step followed by a defatting/disinfecting step. The implantable mesh containing the bone fibers mechanically entangled therein is immersed in acid to effect demineralization. Acids that can be employed in this step include inorganic acids such as hydrochloric acid and as well as organic acids such as formic acid, acetic acid, peracetic acid, citric acid and/or propionic acid. The depth of demineralization into the bone surface can be controlled by adjusting the treatment time, temperature of the demineralizing solution, concentration of the demineralizing solution, and agitation intensity during treatment. Thus, in various embodiments, the DBM may be fully demineralized, partially demineralized, or surface demineralized.

The demineralized bone is rinsed with sterile water and/or buffered solution(s) to remove residual amounts of acid and thereby raise the pH. A suitable defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily, at least about 10 to 40 percent by weight of water (i.e., about 60 to 90 weight percent of defatting agent such as alcohol) is present in the defatting disinfecting solution to produce optimal lipid removal and disinfection within a given period of time. A suitable concentration range of the defatting solution is from about 60 to about 85 weight percent alcohol, or about 70 weight percent alcohol.

In some embodiments, the demineralized bone may be further treated to effect properties of the bone. For example, the DBM may be treated to disrupt the collagen structure of the DBM. Such treatment may comprise collagenase treatment, heat treatment, mechanical treatment, or other. Reference is made to U.S. Provisional Patent Applications 60/944,408; 60/944,417; and 60/957,614, herein incorporated by reference, for further treatment options.

Lyophilization

The bone fibers are lyophilized either in a mold for a desired shape or out of a mold, where it can be shaped (e.g., stamped, punched, cut). For example, the bottle containing bone and conserving agent is initially frozen to −76° C. with the bone and conserving agent later being subjected to a vacuum of less than 100 millitorr while the temperature is maintained at or below −35° C. The end point of the lyophilization procedure is the determination of residual moisture of approximately 5%. Once the bone has been lyophilized, it is stored in sealed, vacuum-contained, bottles prior to its reconstitution and use.

In some embodiments, the demineralization and lyophilization steps alter the shape of the fibers to facilitate mechanical entanglement. To facilitate on-site preparation and/or usage of the implantable mesh, the demineralized fibrous bone elements and non-fibrous bone elements, in some embodiments, in lyophilized or frozen form, and fluid carrier (the latter containing one or more optional ingredients such as those identified above) can be stored in separate packages or containers under sterile conditions and brought together in intimate admixture at the moment of use for immediate application to an osseous defect site employing any suitable means such as spatula, forceps, syringe, tamping device, and the like. Alternatively, the implantable mesh can be prepared well in advance and stored under sterile conditions until required for use. When the implantable mesh is prepared well in advance it is lyophilized, in some aspects, prior to packaging for storage. In some embodiments, the implantable mesh described herein can be combined with autograft bone marrow aspirate, autograft bone, preparations of selected autograft cells, autograft cells containing genes encoding bone promoting action prior to being placed in a defect site. In various embodiments, the implantable mesh is packaged already mixed and ready for use in a suitable container, such as for example, resealable non-toxic bottle, a mesh bag or pouch, or is provided as a kit which can be prepared at a surgeon's direction when needed.

Hydration of Implant

In some embodiments, the implantable mesh containing demineralized bone fibers mechanically entangled therein is hydrated with physiologically acceptable water, physiological saline, sodium chloride, dextrose, Lactated Ringer's solution, phosphate buffered saline, blood, bone marrow aspirate, bone marrow fractions or a combination thereof in an amount sufficient to render the implantable osteogenic material moldable. Once hydrated, the implantable mesh is placed into a surgical site at a location determined by a medical practitioner. The fibers in the implantable mesh maintain their coherency and mechanical interactions such that the mesh does not require a binding agent or carrier when placed in situ. In some embodiments, the fibers of the implantable mesh are hydrophobic and internal or external hydration channels facilitate hydration of the implantable mesh.

In some embodiments, the implantable mesh may be hydrated with PBS or other physiologically acceptable fluid, and provided for use in a hydrated form. The implantable mesh may be placed at a surgical site directly and subsequently hydrated. In some embodiments, the implantable mesh can be wrapped around a bone defect or can help contain other allograft or synthetic material.

A physiologically acceptable liquid, in some embodiments containing water, may be added to the implantable mesh prior to placement into the site or wrapped around the bone defect. Such physiologically acceptable liquids include those discussed above, including physiological saline or a blood product. Blood products include whole blood and blood fractions such as platelet rich plasma and platelet poor plasma.

In some embodiments, the implantable mesh is hydrated with a physiologically acceptable liquid and biocompatible carrier. Non-limiting examples of physiologically acceptable liquids include saline, phosphate buffered saline (PBS), hyaluronic acid, cellulose ethers (such as carboxymethyl cellulose), collagen, gelatin, autoclaved bone powder, osteoconductive carriers, whole blood, blood fractions, bone marrow aspirate, concentrated bone marrow aspirate, and mixtures thereof. Non-limiting examples of blood fractions include serum, plasma, platelet-rich plasma, concentrated platelet-rich plasma, platelet-poor plasma, and concentrated platelet poor plasma. After hydrating, the implantable mesh can be molded into a predetermined shape or administered to or wrapped around a bone defect and manipulated to conform to the bone defect in such a manner that will promote healing. For example, the composition may be hydrated with about 2 ml of saline blood per 2.5 g of combined DBM and periosteal powder.

Methods of Treatment

Illustrative bone repair sites that can be treated with implantable mesh of the disclosure include, for instance, those resulting from injury, defects brought about during the course of surgery, infection, malignancy or developmental malformation. The implantable mesh containing demineralized bone fibers mechanically entangled therein can be used in a wide variety of orthopedic, periodontal, neurosurgical and oral and maxillofacial surgical procedures including, but not limited to the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the implantable mesh include, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

In accordance with certain aspects of the disclosure, the implantable mesh of the disclosure can be used as bone void fillers, or can be incorporated in, on or around load bearing implants such as spinal implants, hip implants (e.g. in or around implant stems and/or behind acetabular cups), knee implants (e.g. in or around stems). In some embodiments, the implantable mesh of the disclosure can be incorporated in, on or around a load-bearing spinal implant device having a compressive strength of at least about 10000 N, such as a fusion cage, PEEK implants, dowel, or other device potentially having a pocket, chamber or other cavity for containing an osteoinductive composition, and used in a spinal fusion such as an interbody fusion. One illustrative such use is in conjunction with a load-bearing interbody spinal spacer to achieve interbody fusion. In these applications, the implantable mesh can be placed in and/or wrapped around the spacer to facilitate the fusion.

Methods for preparing DBM are well known in the art as described, for example, in U.S. Pat. Nos. 5,314,476; 5,507,813; 5,073,373; and 5,405,390, each incorporated herein by reference. Methods for preparing ceramic powders of calcium phosphate and/or hydroxyapatite are described, e.g., in U.S. Pat. Nos. 4,202,055 and 4,713,076, each incorporated herein by reference.

In some embodiments, the method comprises obtaining the fibers by shaving, milling, or pressing the sheet or block under aseptic conditions. The shape of the fibers can be optimized for inducing new bone formation and handling properties via the network of fibers.

In a still further aspect, the present disclosure provides a method of accelerating bone formation at an implantable tissue regeneration scaffold. In a still further aspect, the present disclosure provides a method of regenerating bone in a patient in need thereof, comprising implanting the patient with the implantable mesh.

In a still further aspect, the present disclosure provides a method of treating a bone defect caused by injury, disease, wounds, or surgery utilizing an implantable mesh of this disclosure comprising a combination of fibers of demineralized bone matrix obtained from allograft bone, and fibers of non-allograft bone material, the fibers of non-allograft bone material comprising non-fibrous demineralized bone particles embedded within or disposed on the fibers of non-allograft bone material, all mechanically entangled into the implantable mesh.

It should be understood that the forgoing relates to exemplary embodiments of the disclosure and that modifications may be made without departing from the spirit and scope of the disclosure as set forth in the following claims.

What is claimed is:

1. A method of preparing an implantable mesh, the method comprising providing a plurality of biodegradable polymer mesh fibers as a base mesh layer; needle punching a plurality of demineralized bone fibers onto the plurality of biodegradable polymer mesh fibers such that the plurality of demineralized bone fibers are disposed within the base mesh layer; and mechanically entangling the demineralized bone fibers into the base mesh layer along a longitudinal axis of the base mesh layer forming the implantable mesh.

2. A method of claim 1, wherein the mechanical entangling comprises applying needle punching with barbed needles, spun lacing, entanglement with water jets or air jets or ultrasonic entanglement with ultrasonic waves.

3. A method of claim 2, wherein the mechanical entangling further comprises applying to the implantable mesh moisture, heat and/or pressure provided by pressure rollers.

4. A method of claim 1, wherein (i) the mesh is porous having pores from about 100 to about 200 μm; (ii) the mesh does not contain a carrier; or (iii) the mesh is woven, non-woven, knitted, wrapped, plied, braided or a mixture thereof.

5. A method of claim 1, wherein the demineralized bone fibers have (i) an aspect ratio of from about 50:1 to about 1000:1; (ii) a diameter from about 100 µm to about 2 mm; or (ii) a length from about 0.5 cm to about 10 cm.

6. A method of claim 1, wherein the biodegradable polymer mesh fibers comprise a bioerodible polymer having a molecular weight from about 1,000 Daltons to about 30,000 Daltons, the plurality of demineralized bone fibers comprising from about 20% to about 60% by weight of the implantable mesh.

7. A method of claim 1, wherein the implantable mesh does not contain a carrier or an adhesive.

8. A method of claim 1, wherein the needle punched implantable mesh comprises a plurality of layers in the implantable mesh.

9. A method of claim 1, further comprising forming the implantable mesh into a sheet, plate, disk, tunnel, cone or tube.

10. A method of claim 1, wherein the implantable mesh comprises (i) natural materials, synthetic polymeric resorbable materials, synthetic polymeric non-resorbable materials or mixtures thereof; or (ii) carbon fiber, metal fiber, polyetheretherketones, nonresorbable polyurethanes, polyethers, polyethylene terephthalate, polyethylene, polypropylene, Teflon or mixtures thereof.

11. A method of claim 10, wherein the synthetic polymer resorbable materials comprise poly(lactic acid) (PLA), poly(glycolic acid) (PGA), poly(lactic acid-glycolic acid) (PLGA), polydioxanone, PVA, polyurethanes, polycarbonates, polyhydroxyalkanoates (polyhydroxybutyrates and polyhydroxyvalerates and copolymers), polysaccharides, polyhydroxyalkanoates polyglycolide-co-caprolactone, polyethylene oxide, polypropylene oxide, polyglycolide-co-trimethylene carbonate, poly(lactic-co-glycolic acid) or mixtures thereof.

12. A method of claim 10, wherein the natural materials comprise silk, extracellular matrix, demineralized bone fibers, collagen, ligament, tendon tissue, silk-elastin, elastin, collagen, cellulose or mixtures thereof.

13. A method of claim 1, wherein the implantable mesh further comprises a plurality of surface demineralized bone fibers, bone chips, bone particles or mixtures thereof inside the implantable mesh.

14. A method of claim 1, wherein the implantable mesh further comprises (i) an osteinductive and/or osteopromotive additive including a bone marrow aspirant, blood, a blood product, a bone morphogenetic protein, a growth factor disposed on the biodegradable mesh fiber, (ii) a therapeutic agent or mixtures thereof; or (iii) collagen fibers mechanically entangled into the mesh.

15. A method of claim 1, wherein the implantable mesh further comprises one or more synthetic resorbable ceramics having a tricalcium phosphate:hydroxyapatite weight ratio of about 50:50 to about 95:5.

* * * * *